| United States Patent [19] | [11] Patent Number: 4,606,939 |
| Frank et al. | [45] Date of Patent: Aug. 19, 1986 |

[54] SMALL PARTICLE FORMATION

[75] Inventors: Sylvan G. Frank, Columbus, Ohio; Arne F. Brodin, Sodertalje, Sweden; Chih-Ming J. Chen, East Syracuse, N.Y.; Ratnesh Shrivastava, Columbus, Ohio

[73] Assignee: The Ohio State University Research Foundation, Columbus, Ohio

[21] Appl. No.: 621,133

[22] Filed: Jun. 15, 1984

Related U.S. Application Data

[63] Continuation-in-part of Ser. No. 506,598, Jun. 22, 1983, abandoned.

[51] Int. Cl.[4] .............................................. B01J 13/02
[52] U.S. Cl. ................................. 427/213.3; 252/303; 252/363.5; 424/31; 514/962; 514/965
[58] Field of Search ...................... 427/213.35, 213.36, 427/213.3; 424/33, 35, 37, 365; 23/302 A, 302 T; 252/303, 363.5; 514/965

[56] References Cited

U.S. PATENT DOCUMENTS 3,037,849  6/1962  Frint et al. ..................... 23/302 T X
3,574,132  4/1971  Mosier et al. ..................... 424/37 X
3,725,014  4/1973  Poncha et al. ................. 23/302 T X

OTHER PUBLICATIONS

McCutcheon's Detergents and Emulsifiers, 1973 No. American Edition, Publ. by McCutcheons's Divison, Allured Publishing Corp., Ridgewood, N.J, 1973, p. 173.

W. L. Chiou et al., "Enhancement of Dissolution Rates of Poorly Water-Soluble Drugs by Crystallization in Aqueous Surfactant Solutions . . . ", J. Pharm. Sci., 65, 1702–1704 (1976).

K. Ikeda et al., "Micellar Interaction of Tetracycline Antibiotics", Chem. Pharm. Bull., 25, 106701072 (1977).

V. K. La Mer et al.: "Theory Production and Mechanism of Formation of Monodispersed Hydrosols", J. Amer. Chem. Soc., 72, 4847–4854 (1950).

P. L. Madan: "Microencapsulation: I. Phase Separation or Coaceryation", Drug Development and Industrial Pharmacy, 4, 95–116 (1978).

P. L. Madan: "Microencapsulation: II. Interfacial Reactions", Drug Development and Industrial Pharmacy, 4, 289–304 (1978).

P. L. Madan: "Clofibrate Microcapsules: III. Mechanism of Release", Drug Development and Industrial Pharmacy, 6, 629–644 (1980).

H. P. Merckle et al., "Preparation and In Vitro Evaluation of Cellulose Acetate Phthalate Coacervate Microcapsules", J. Pharm. Sci., 62, 1444–1448 (1973).

A. S. Michaels et al.: "The Effect of Surface Active Agents on Crystal Growth Rate and Crystal Habit", J. Phys. Chem., 64, 13–19 (1960).

G. I. Mukhayer et al.: "Interactions Between Large Organic Ions of Opposite Charge: VI. Coacervation . . . ", J. Coll. and Int. Sci., 66, 110–117 (1978).

J. R. Nixon et al.: "The In Vitro Evaluation of Gelatin Coacervate Microcapsules", J. Pharm. Pharmac., 23, 147S–155S (1971).

O. Siddiqui et al.: "Physical Factors Affecting Microencapsulation by Simple Coacervation of Gelatin", J. Phar. Pharmacol., 35, 70–73 (1983).

Chih-Ming James Chen: "Production of Drugs in Small Particle Form", Dissertation, The Ohio State University, 1981.

Primary Examiner—Richard D. Lovering

[57] ABSTRACT

The present invention is concerned with the simultaneous formation and encapsulation of small particles of organic compounds whose solubility in water is greater at a first pH than at a second pH by concurrently precipitating said organic compounds as small particles and forming a coacervate of an anionic (or cationic) surfactant and an amphoteric surfactant. The process is preferably used to prepare a readily soluble encapsulated pharmaceutically active compound.

9 Claims, No Drawings

SMALL PARTICLE FORMATION

This application is a continuation-in-part of U.S. patent application Ser. No. 506,598 filed June 22, 1983 and now abandoned.

The present invention is concerned with the formation of small particles of organic compounds upon precipitation at a selected temperature in the presence of a surfactant mixture, induced by pH change from a first pH at which their solubility in water is greater to a second pH at which it is lower. In this application, a small particle refers to a particle size of less than 2 µm. The object of the invention is to provide a process for the formation of small particles of organic compounds especially pharmaceutically active compounds.

The rate and extent of absorption of a pharmaceutically active compound by a patient is dependent on the particle size of the compound. The administration of pharmaceutically active compounds having smaller particles makes it possible to give a reduced dosage at lower cost and results in fewer side effects.

BACKGROUND OF THE INVENTION

From a pharmaceutical point of view, the smaller the particle size of a relatively insoluble drug, the greater is its rate of solution and as a rule, the greater is its bioavailability, (J. H. Fincher, J. Pharm. Sci., 57, 1825 (1968)). To this end, small particles are conventionally formed by mechanical subdivision of bulk matter or by aggregation of small molecules or ions, (D. J. Shaw, "Introduction to Colloid and Surface Chemistry" 3rd Edition, Butterworths, London, 1980, Chapter 1). The initial rate of nucleation depends on the relative degree of supersaturation of the solute, while the rate of particle growth depends on several factors, including the amount of material available, the viscosity of the medium, adsorption of impurities onto the particle surface and particle-particle interaction, (D. J. Shaw, "Introduction to Colloid and Surface Chemistry", 3rd Edition, Butterworths, London, 1980, Chapter 1). The coacervation of ionic dyes with ionic surfactants has been reported, (S. P. Moulik, S. Ghosh and A. R. Das, Colloid & Polymer Sci., 257, 645 (1979); B. W. Barry and G. F. J. Russell, J. Pharm. Sci., 61, 502 (1972)).

SUMMARY OF THE INVENTION

A method has now been found which is useful for forming small particles of weakly acidic and weakly basic organic compounds upon precipitation at a selected temperature in the presence of a surfactant mixture, induced by pH change from a first pH at which their solubility in water is greater to a second pH at which it is lower. The method comprises the steps of:

(a) dissolving the compound in water, when said compound is weakly acidic, in the presence of sufficient base to raise the pH of the solution to said first pH, and above the pKa of the compound, preferably about 2 pH units together with an anionic surfactant which maintains its ionic condition between said first pH and said second pH and an amphoteric surfactant which is anionic at said first pH and whose cationic nature increases as the pH is changed from the first pH to said second pH. When said compound is weakly basic, in the presence of sufficient acid to lower the pH to said first pH below the pKa of said compound, preferably about 2 pH units together with a cationic surfactant which maintains its ionic condition between said first pH and said second pH, and an amphoteric surfactant which is cationic at said first pH and whose anionic nature increases as the pH is changed from the first pH to said second pH;)

(b) stirring and titrating the solution, with a suitable acid titrant (if the starting solution is basic) or a suitable basic titrant (if the starting solution is acidic) in an amount effective to alter the pH from said first pH to said second pH and thereby cause the concurrent formation of a coacervate of the surfactants, and precipitation of the compound as small particles.

The said second pH may be about 2 pH units above or below the pKa of the compound to precipitate the free acid, free base or the salt forms of the compound.

It is believed that as the pH of the solution changes, the compound's solubility is altered and a coacervate forms between the anionic or cationic surfactant (as the case may be) and the amphoteric surfactant simultaneously with the precipitation of the compound.

DETAILED DESCRIPTION OF THE INVENTION

This process is preferably used to form small particles of organic compounds whose solubility in water is greater at a first pH than at a second pH. Such compounds are commonly found in the pharmaceutical industry and are preferably used in small-particle form as explained above.

Depending on the protolytic properties of such an organic compound it can be dissolved in either an alkaline (weakly acidic compound) or acidic solution (weakly basic compound) and precipitated by the subsequent titration with either an acid or alkaline titrant, respectively. The starting pH should preferably be 2 pH units above the pKa of a weakly acid compound and preferably 2 pH units below the pKa of a weakly basic compound.

Suitable pharmaceutically active compounds which can be used in this process are, for example, sulfadiazine, lidocaine, salicyclic acid, felodipine, sulbactam pivoxil, chlorzoxazone, theophylline and erythromycin. Suitable amphoteric surfactants which change ionic character between the first and second pH are, for example, surfactants derived from fatty imidazolines (Miranols ), particularly monocarboxylated compounds, such as Miranol SM, which is a clear, aqueous, amphoteric solution, derived from 99% capric acid; the surfactant is a monocarboxylated derivative of a capryl imidazoline. Other suitable amphoteric surfactants are, for example, betaines, such as cocamidopropyl betaine, lauramidopropyl, betaine, amino acid amphoterics such as disodium lauriminodipropionate and imidazoline derived amphoterics such as Miranol SM and other members of these general classes.

Suitable anionic surfactants which maintain their ionic condition between the first and second pH of the weakly acidic organic compounds are, the common salts of natural and synthetic organic carboxylates, sulfonates and sulfates, such as for example, sodium or potassium stearates, sodium lauryl sulfate, sodium or potassium alkyl sulfates having alkyl groups with 8–18 carbon atoms and dialkyl sodium sulfosuccinates having alkyl groups with 6–8 carbon atoms.

Suitable cationic surfactants which maintain their ionic condition between the first and second pH of the weakly basic organic compounds are common surface-active derivatives of ammonium and various amines, for example, alkyltrimethylammonium halides containing alkyl groups with 11–18 carbon atoms, alkylpyridinium halides containing alkyl groups with 8–18 carbon atoms, benzylalkyldimethylammonium halides containing alkyl groups with 8–18 carbon atoms, and alkyldimethylethylammonium halides containing alkyl groups with 8–18 carbon atoms.

A suitable molar ratio of the pharmaceutically active compound to amphoteric surfactant and the anionic or cationic surfactant is for example 0.15:1:1 to 4.4:1:1, up to the maximum solubilizing capacity for a particular system.

The alkaline solution used to dissolve the weakly acidic compounds can be, for example, sodium hydroxide or potassium hydroxide solutions. The alkaline solution should be about 0.05–5.0 N, preferably 0.05 N or 0.1 N in order to obtain a pH preferably 2 units above the pKa of the compound. For dissolving the weakly basic compounds, the acidic solutions should be 0.05–5.0N, preferably 0.05N or 0.1N in order to obtain a pH preferably 2 units below the pKa of the compound.

The titrations are performed with stirring using a suitable acid titrant, such as hydrochloric acid to reduce the pH of the solution to anywhere below pH 9 to pH 1.5, or in the case of an alkaline titrant, to a pH anywhere above pH 2 up to pH 12 and to cause the concurrent formation of a coacervate of the surfactants and precipitation of the compounds as small particles.

The molarity of the acid titrant should be in the range 0.05–5.0N, preferably 0.1N or 1.0N, and that of the alkaline titrant should be in the range of 0.05–5.0N, preferably 0.2N or 1.0N. Higher normalities can be used as well to obtain the desired pH.

The titration should be preformed within the temperature range of 0°–50° C., usually at about 22° C.

While the invention is described with particular reference to pharmaceutical manufacture, it should be understood that the basic principals are not so limited. Obviously when applied to pharmaceuticals, the surfactants, acids and bases used should not leave pharmaceutically objectionable residues.

EXAMPLE 1

Appropriate molar amounts of sulfadiazine, sodium lauryl sulfate and Miranol SM (42–44% solids by weight) as indicated in Table 1 were dissolved in sodium hydroxide solution, 0.05N NaOH, when 0.044M or 0.0044M sulfadiazine was used or 0.1N, for 0.088M sulfadiazine. The solutions were then stirred at constant speed with a magnetic stirrer and sulfadiazine was precipitated upon dropwise titration of the solutions with 1.0N hydrochloric acid solution.

The effect of several different composite ratios of sulfadiazine, Miranol SM and sodium lauryl sulfate on the precipitation of sulfadiazine is summarized in Table 1. As a general rule, precipitation of the sulfadiazine began when the pH reached 8.5–8.6, as indicated by increasing turbidity. Samples 1–5 represent the process of this invention while Sample A does not.

TABLE 1

Precipitation of Sulfadiazine Upon Acidification of Alkaline Solutions Containing Surfactants

| Sample | Sulfadiazine:Miranol SM:Sodium Lauryl Sulfate Molar ratio | Concentration ratio | pH of appearance of turbidity | Observations of precipitate upon acidification to pH 4. |
|---|---|---|---|---|
| 1 | 1:1:1 | 0.044 M:0.045 M:0.045 M | 8.5–8.6 | Rod-shaped particles and needles, 1–12 μm Oval-shaped particles <1 μm Droplets of coacervate phase entrapping some particles |
| 2 | 1:2:2 | 0.044 M:0.09 M:0.09 M | 8.5–8.6 | Rod- and oval-shaped particles <1 μm. Larger rods up to 4 μm Droplets of coacervate phase entrapping some particles |
| 3 | 2:2:2 | 0.088 M:0.09 M:0.09 M | ~8.9 | small oval- or rod-shaped particles 1 μm |
| 4 | 2:1:1 | 0.088 M:0.045 M:0.045 M | ~8.9 | small oval- or rod-shaped particles <1 μm |
| 5 | 4.4:1:1 | 0.088 M:0.02 M:0.02 M | ~8.9 | small oval- or rod-shaped particles <1 μm |
| A | 0.1:1:1 | 0.0044 M:0.045 M:0.045 M | 6.8–7.0 | large needle shaped crystal of sulfadiazine (10–30 μm) |

We claim:

1. A process for forming small particles of a weakly acidic organic compound whose solubility in water is greater at a first pH than at a second pH which process comprises:
   (a) dissolving said compound in water in the presence of sufficient base to raise the pH to said first pH and preferably about 2 pH units above the pKa of the compound, together with an anionic surfactant which maintains its ionic condition between the first and second pH and an amphoteric surfactant whose cationic nature increases from the first pH to said second pH; and
   (b) stirring and titrating the solution, with a titrant effective to reduce the pH of said solution to said second pH to cause the concurrent formation of a coacervate of the anionic and amphoteric surfactants, and precipitation of the compound as small particles.

2. A process according to claim 1, wherein the anionic surfactant is selected from the group consising of sodium lauryl sulfate, sodium alkyl sulfates having alkyl groups containing 8–18 carbon atoms and dialkyl sodium sulfosuccinates having alkyl groups containing 6–8 carbon atoms.

3. A process for forming small particles of a weakly basic organic compound whose solubility in water is greater at a first pH than at a second pH which process comprises:
   (a) dissolving said compound in water in the presence of sufficient acid to lower the pH to said first pH and preferably about 2 pH units below the pKa of the compound, together with a cationic surfactant which maintains its ionic condition between the first and second pH and an amphoteric surfactant whose anionic nature increases from the first pH to said second pH; and (b) stirring and titrating the solution, with a titrant effective to raise the pH of said solution to said second pH to cause the concurrent formation of a coacervate of the cationic and amphoteric surfactants, and precipitation of the compound as small particles.

4. A process according to claim 3, wherein the cationic surfactant is selected from the group consisting of alkyltrimethylammonium halides containing alkyl groups containing 11–18 carbon atoms, alkylpyridinium halides containing alkyl groups containing 8–18 carbon atoms, benzylalkyldimethylammonium halides containing alkyl groups with 8–18 carbon atoms and alkyldimethylammonium halides containing alkyl groups containing 8–18 carbon atoms.

5. A process according to claim 1 or 3, wherein the compound is pharmaceutically active.

6. A process according to claim 5, wherein the pharmaceutically active compound is selected from the group consisting of sulfadiazine, lidocaine, salicylic acid, felodipine, sulbactam pivoxil, chlorzoxazone, theophylline and erythromycin.

7. A process according to claims 1 or 3, wherein the ratio of compound to amphoteric surfactant and the cationic or anionic surfactant is about 0.15:1:1 to 4.4:1:1, and up to the maximum solubilizing capacity for a particular system.

8. The process according to claim 1 or 3 wherein the amphoteric surfactant is selected from the group consisting of imidazoline derived amphoterics, betaines and amino acid amphoterics.

9. A process according to claims 8, wherein the amphoteric surfactant is selected from the group consisting of cocamidopropyl betaine, lauramidopropyl betaine, disodium and lauriminodipropionate.

* * * * *

UNITED STATES PATENT AND TRADEMARK OFFICE
CERTIFICATE OF CORRECTION

PATENT NO. : 4,606,939

DATED : August 19, 1986

INVENTOR(S) : Frank et al.

It is certified that error appears in the above-identified patent and that said Letters Patent is hereby corrected as shown below:

Col. 1, line 55, "when" should read --(When--;

Col. 2, line 51, delete the comma before "betaine";

Col. 3, line 53, "0.2N" should read --0.1N--;

Col. 3, line 55, "preformed" should read --performed--;

Col. 3, line 59, "principals" should read --principles--;

Col. 4, lines 43-44, "preferably about 2 pH units above the pKa of the compound" should read --above the pKa of the compound preferably about 2 pH units--;

Col. 4, lines 67-68, "preferably about 2 pH units below the pKa of the compound" should read --below the pKa of the compound preferably about 2 pH units.

Signed and Sealed this

Twelfth Day of September, 1989

Attest:

DONALD J. QUIGG

Attesting Officer

Commissioner of Patents and Trademarks